(12) United States Patent
Sal et al.

(10) Patent No.: US 8,822,420 B2
(45) Date of Patent: Sep. 2, 2014

(54) PEPTIDES AND APTAMERS THEREOF AS SPECIFIC MODULATORS OF MUTANT P53 FUNCTION

(75) Inventors: Giannino Del Sal, Trieste (IT); Elisa Guida, Trieste (IT); Andrea Bisso, San Daniele del Friuli (IT)

(73) Assignee: Universita Degli Studi di Trieste, Trieste (IT)

( * ) Notice: Subject to any disclaimer, the term of this patent is extended or adjusted under 35 U.S.C. 154(b) by 542 days.

(21) Appl. No.: 12/921,954

(22) PCT Filed: Mar. 13, 2008

(86) PCT No.: PCT/EP2008/053010
§ 371 (c)(1),
(2), (4) Date: Sep. 10, 2010

(87) PCT Pub. No.: WO2009/112075
PCT Pub. Date: Sep. 17, 2009

(65) Prior Publication Data
US 2012/0258920 A1 Oct. 11, 2012

(51) Int. Cl.
A61K 38/10 (2006.01)
A61P 35/00 (2006.01)
C07K 7/08 (2006.01)
G01N 33/68 (2006.01)

(52) U.S. Cl.
CPC *G01N 33/68* (2013.01); *C07K 7/08* (2013.01); G01N 2333/4748 (2013.01)
USPC .......................................... 514/19.3; 530/326

(58) Field of Classification Search
None
See application file for complete search history.

(56) References Cited

PUBLICATIONS

Green, Biochemistry, vol. 45, p. 12547-12559, 2006.*
Mendoza, Arch. Immunol. Ther. Exp., vol. 53, p. 47-60, 2005.*
Soussi, T., "p53 alterations in human cancer: more questions than answers"; Oncogene (2007) 26 pp. 2145-2156.
Vogelstein, Bert et al., "Surfing the p53 network"; Nature, vol. 408; Nov. 16, 2000; pp. 307-310.
Murray-Zmijewski, F. et al.; "p53/p73 isoforms: an orchestra of isoforms to harmonise cell differentiation and response to stress"; Cell Death and Differentiation; (2006); 13; pp. 962-972.
Joerger, AC, et al.; "Structure-function-rescue: the diverse nature of common p53 cancer mutants"; Oncogene; (2007) 26; pp. 2226-2242.
Sigal, Alex et al.; "Oncogenic Mutations of the p53 Tumor Suppressor: The Demons of the Guardian of the Genome"; Cancer Res; 2000; 60; pp. 6788-6793.
Iwakuma, T. et al.; "Crippling p53 activities via knock-in mutations in mouse models"; Oncogene; (2007); 26; pp. 2177-2184.
Lang, Gene A., et al.; "Gain of Function of a p53 Hot Spot Mutation in a Mouse Model of Li-Fraumeni Syndrome"; Cell, vol. 119; Dec. 17, 2004; pp. 861-872.

Olive, Kenneth P., et al; "Mutant p53 Gain of Function in Two Mouse Models of Li-Fraumeni Syndrome"; Cell, vol. 119, Dec. 17, 2004; pp. 847-860.
Hingorani, Sunil R. et al.; "Trp53R172H and KrasG12D cooperate to promote chromosomal instability and widely metastatic pancreatic ductal adenocarcinoma in mice"; Cancer Cell; May 2005; vol. 7; pp. 469-483.
Bossi, G. et al.; "Mutant p53 gain of function: reduction of tumor malignancy of human cancer cell lines through abrogation of mutant p53 expression"; oncogene; (2006); 25; pp. 304-3309.
Weisz, L. et al.; "Transcription regulation by mutant p53"; Oncogene; (2007); 26; pp. 2202-2211.
Li, Y et al.; "Are interactions with p63 and p73 involved in mutant p53 gain of oncogenic function?"; Oncogene (2007); 26; pp. 2220-2225.
Song, Hoseok et al; "p53 gain-of-function cancer mutants Induce genetic Instability by inactivating ATM"; Nature Cell Biology, vol. 9; No. 5; May 2007; pp. 573-588.
Colas, Pierre et al.; "Genetic selection of peptide aptamers that recognize and inhibit cyclin-dependent kinase 2"; Nature; vol. 380; Apr. 11, 1996; pp. 548-550.
Dinnen, Richard D. et al.; "Activation of Targeted Necrosis by a p53 Peptide a Novel Death Pathway That Circumvents Apoptotic Resistance"; Journal of Biological Chemistry; Sep. 14, 2007; vol. 282; No. 37; pp. 26675-26686.
Kabouridis, S. Panagiotis; "Biological applications of protein transduction technology"; Trends in Biotechnology; vol. 21, No. 11; Nov. 2003; pp. 498-503.
Woodman, Robbie et al.; "Design and Validation of a Neutral Protein Scaffold for the Presentation of Peptide Aptamers"; J. Mel. Biol. (2005) 352; pp. 1118-1133.
Bourdon, Jean-Christophe et al.; "p53 isoforms can regulate p53 transcriptional activity"; Genes & Development; 19; (2005) pp. 2122-2137.
Colas, Pierre et al.; "Targeted modification and transportation of cellular proteins"; PNAS; vol. 97; No. 25; Dec. 5, 2000; pp. 13720-13725.
Joerger, Andreas C. et al; "Crystal Structure of a Superstable Mutant of Human p53 Care Domain"; The Journal of Biological Chemistry; vol. 279; No. 2; Jan. 9, 2004; pp. 1291-1296.
Evans, David et al.; "Electrical protein detection in cell lysates using high-density peptide-aptamer microarrays"; J. Biol.; 2008; vol. 7; Article 3; pp. 3.1-3.11.

(Continued)

*Primary Examiner* — Misook Yu
*Assistant Examiner* — Michael D Allen
(74) *Attorney, Agent, or Firm* — Gifford, Krass, Sprinkle, Anderson & Citkowski, P.C.

(57) ABSTRACT

In the present application isolated peptides and aptamers thereof able to interact with structural and conformational p53 mutants within the region of the wild-type p53 DNA binding core domain comprised from amino acids 74 to amino acids 298 using the yeast two-hybrid method are disclosed. These PAs are able to efficiently recognize several different p53 point mutants but not wild-type p53. Therefore the peptides and aptamers identified can be useful as inhibitors of mutant p53-associated pro-oncogenic functions for anticancer therapy or as diagnostic tools for mut-p53 or wild-type p53 or as template for designing new peptido-mimetic drugs able to specifically target tumor cells.

8 Claims, 7 Drawing Sheets

(56) References Cited

PUBLICATIONS

Selivanova, G. et al., "Reactivation of mutant p53: molecular mechanisms and therapeutic potential", Oncogene, vol. 26, No. 15, Apr. 2007, pp. 2243-2254.

Bykov, V.J.N. et al.; Restoration of the tumor suppressor function to mutant p53 by a low-molecular-weight compound, Nature Medicine, Nature publishing Goup, New York, NY, vol. 8, No. 3, Mar. 1, 2002, pp. 282-288.

Gostissa, Monica et al, "The transcriptional repressor hDaxx potentiates p53-dependent apoptosis", Jounal of Biological Chemistry, vol. 279, No. 46, Nov. 12, 2004, pp. 48013-48023.

Gostissa, Monica et al., "Activation of p53 by conjugation to the ubiquitin-like protein SUMO-1", EMBO (European Molecular Biology Organization) Journal, vol. 18, No. 22, Nov. 15, 1999, pp. 6462-6471.

Hoppe-Syler, F. et al., "Peptide Aptamers: Specific Inhibitors of Protein Function", Current Molecular Medicine, Bentham Science Publishers, vol. 4, No. 5, Aug. 1, 2004, pp. 529-538.

Guida, Elisa et al, "Peptide aptamers targeting mutant p53 induce apoptosis in tumor cells", Cancer Research, Aug. 15, 2008, vol. 68, No. 16, Aug. 15, 2008, pp. 6550-6558.

\* cited by examiner

PEPTIDES AND APTAMERS THEREOF AS SPECIFIC MODULATORS OF MUTANT P53 FUNCTION

CROSS-REFERENCE TO RELATED APPLICATIONS

This application is the U.S. national phase of PCT/EP2008/053010 filed Mar. 13, 2008.

FIELD OF THE INVENTION

The present invention relates to new peptides and aptamers thereof able to modulate the mutant p53 function by binding contact and conformational p53 mutants within the region corresponding to wild-type p53 DNA binding core domain and use thereof.

BACKGROUND OF THE INVENTION

Most tumors are characterized by impairment of p53 pathway, either by mutation of the p53 gene (TP53) (Soussi, T. p53 alterations in human cancer: more questions than answers. *Oncogene*, 2007, 26:2145-56), or by deregulation of other components of the pathway (Vogelstein, B., Lane, D., Levine, A. J. Surfing the p53 network. *Nature*, 2000, 408 (6810):307-10).

The importance of p53 function as a tumor suppressor is underlined by the fact that at least 50% of human tumors carry mutations in TP53. Interestingly, the majority of the TP53 alterations are missense mutations leading to the expression of full-length point mutants (hereinafter identified also as mut-p53 or mutant p53) that accumulate to high levels in tumor cells and show a prolonged half life compared to wild-type protein p53 (herein after also as wt p53).

The determinant role of p53 as tumor suppressor is related to the fact that p53 is a transcription factor that, in response to stress signals, becomes activated and determines different cellular outcomes, as temporary growth arrest and DNA repair, irreversible growth arrest or apoptosis. Furthermore, p53 activity is tightly regulated by several coordinated mechanisms that ensure proper activation including post-translational modifications, as well as interaction with protein partners that modulate its function (Vogelstein, B. et al. 2000, ref. cit.).

The protein p53 may be divided into three functional domains, an N-terminal transactivation domain (hereinafter identified also as TAD), a central DNA binding core domain (hereinafter identified also as CD), comprised from the amino acids (aa) 94 to 298, and a C-terminal oligomerization domain (hereinafter identified also as OLD). Due to multiple splicing, alternative promoter and alternative initiation of translation p53 is also present in several isoforms (Murray-Zmijewski, F., Lane, D. P. and Bourdon, J. C. p53/p63/p73 isoforms: an orchestra of isoforms to harmonise cell differentiation and response to stress. *Cell death and differentiation*, 2006, 13:962-972). The modular structure of p53 is also shared by the other p53 family members, such as p63 and p73, that are also present within the cells in several isoform (Murray-Zmijewski, F. et al., 2006, ref. cit.). Most frequently, tumor-associated mutations are found in the CD. As a consequence of these mutations, the ability of the protein to recognize p53 responsive elements (RE) on DNA is lost and mutant proteins are defective for wild-type function (Joerger, A. C. & Fersht, A. R. Structure-function-rescue: the diverse nature of common p53 cancer mutants. *Oncogene*, 2007, 26:2226-42). According on the effect of mutations on protein structure, p53 mutants were classified as contact mutants, when an amino acid directly involved in protein-DNA interaction is mutated, or conformational mutants, when mutations alter protein conformation without affecting amino acids involved in DNA binding.

Basing on the high frequency of mutation and on the observation that p53 point mutants are highly abundant in tumors, it was proposed that mutant proteins may play an active role in tumorigenesis. Indeed, the expression of p53 point mutants was shown to favor tumorigenesis and this oncogenic function has been explained by both trans-dominant suppression of wt p53 activities and by the acquisition of novel properties by mutant proteins, commonly referred to as gain-of-function (GOF) (Sigal, A., and Rotter, V. Oncogenic mutations of the p53 tumor suppressor: the demons of the guardian of the genome. *Cancer Res.*, 2000, 60:6788-6793). This is supported by several experimental findings indicating that p53 point mutants exert distinct tumorigenic activities independently of wt p53 inhibition. Mutant p53 GOF has been associated with enhanced tumorigenic potential in mice, increased proliferation and resistance to drugs commonly used in anti-cancer therapy (Iwakuma, T. and Lozano, G. Crippling p53 activities via knock-in mutations in mouse models. *Oncogene*, 2007, 26:2177-2184). In addition, mouse models have provided evidence for a role of mutant p53 in altering tumor spectrum and increasing the metastatic potential of tumors cells (Lang, G. A., Iwakuma, T., Suh, Y. A. et al. Gain of function of a p53 hot spot mutation in a mouse model of Li-Fraumeni syndrome. *Cell*, 2004, 119(6):861-72; Olive, K. P., Tuveson, D. A., Ruhe, Z. C., et al. Mutant p53 gain of function in two mouse models of Li-Fraumeni syndrome. *Cell*, 2004, 119(6):847-60; Hingorani, S. R., Wang, L., Multani, A. S. et al. Trp53R172H and KrasG12D cooperate to promote chromosomal instability and widely metastatic pancreatic ductal adenocarcinoma in mice. *Cancer Cell*, 2005, 7(5):469-83). Conversely, ablation of mutant p53 expression in human tumor-derived cell lines reduced proliferation, survival, chemoresistance and tumorigenicity (Bossi, G., Lapi, E., Strano, S., Rinaldo, C., Blandino, G., Sacchi, A. Mutant p53 gain of function: reduction of tumor malignancy of human cancer cell lines through abrogation of mutant p53 expression. *Oncogene*, 2006, 25(2):304-9)

The mechanisms underlying mutant p53 GOF remain largely unclear, nevertheless recent experimental findings have shown that mutant p53 is involved in precise cellular events. Mutant p53 was shown to alter the expression of several genes involved in cell proliferation, most likely by modifying the activities of other transcription factors (Weisz, L., Oren, M., and Rotter, V. Transcription regulation by mutant p53. *Oncogene*, 2007, 26: 2202-2211).

In addition, p53 mutants form aberrant protein complexes with several proteins such as p73, p63 and Mre11 (Li, Y., and Prives, C. Are interactions with p63 and p73 involved in mutant p53 gain of oncogenic function? *Oncogene*, 2007, 26:2220-2225.; Song, H., Hollstein, M., Xu, Y. p53 gain-of-function cancer mutants induce genetic instability by inactivating ATM. *Nat. Cell Biol.*, 2007, 9(5):573-80) interfering with their ability to induce apoptosis or a proficient DNA damage response respectively.

Given the active role of mutant p53 in tumorigenesis, it represents an interesting target for the development of anti-cancer therapies. Furthermore, since p53 is often mutated only in tumor cells and not in the adjacent normal tissue, a strategy based on inactivation of its pro-oncogenic function would be highly selective. Indeed, some approaches aimed to restore wild-type function to p53 mutants leaded to the identification of small molecules, such as CP-31398 and PRIMA-1 (Selivanova, G. and Wiman, K. G. Reactivation of mutant p53: molecular mechanisms and therapeutic potential. *Oncogene*, 2007, 26:2243-2254), able to selectively induce massive apoptosis in cells expressing mutant p53.

More recently in WO 2006/054138 another approach to ablate the oncogenic gain-of-function of mutant p53 is disclosed. The purpose in this case has been pursued through a group of small (8-10 aa) peptides able to break the complexes between the mutant p53 and p63, p73 and the respective isoform proteins, increasing in this way the free p73 and p63 and therefore restoring the oncosuppressor activity of these proteins.

However, given the active role of p53 mutants in promoting tumorigenesis, the need to identify various strategies, being able to inactivate their tumorigenic function or to restore wild-type function of p53, in order to find out new very selective and efficient chemotherapeutic treatments of tumors is still strongly felt.

SUMMARY OF THE INVENTION

In pursuing the purpose to provide a new approach for the treatment of tumors by acting on p53 mutant function, the Inventors have found that new peptides or aptamers thereof (hereinafter PAs) that selectively bind p53 contact (hereinafter also indicated as structural mutants) and conformational mutants in the region corresponding to wild-type p53 DNA binding core domain can induce death of tumor cells bearing mut-p53.

Therefore, the object of the present invention are molecules comprising peptides or aptamers thereof capable to bind contact and conformational p53 mutants or isoforms thereof within the region corresponding to wild-type p53 DNA binding core domain comprised from amino acids 94 to amino acids 298 sequence. Moreover said peptides or aptmers can also contact the p53 family members p73 and p63.

In particular, said peptides are selected from the group consisting of peptides having the sequences AKYCQ-CAAKVRVTAAM (Seq. ID No 1), GPV-VPRTQYMSLAFGW (Seq. ID No 2), IQITLTG-WSARVTTSG (Seq. ID No 3), VWAESCDDCGEYWRYV (Seq. ID No 4), DVADWESCGEYWCYRV (Seq. ID No 5), QAGSGREKCQHAAYLS (Seq. ID No 6), ARTDTAVVH-VCDSGRQ (Seq. ID No 7), QQSRGRCPSCIPEAAS Seq. ID No 8), PGKLIRVSENMSSALG (Seq. ID No 9), TPEGLDVALAVAAYSV (Seq. ID No 10).

In a preferred aspect the molecules comprising peptides and aptamers thereof object of the invention are functional inhibitors of mutant p53-associated pro-oncogenic functions.

Accordingly to said features, further objects of the present invention are the uses of said molecules comprising peptides or aptamers thereof as:
i) inhibitors of mut-p53-associated pro-oncogenic functions in tumor therapy;
ii) reagents for the detection of p53 mutants;
iii) molecular platform for designing new peptido-mimetic drugs able to specifically target tumor cells bearing mut-p53;
iv) carriers for molecular targeting antitumoral drugs to mut-p53 bearing tumoral cells;
v) reagents for binding and modulating p73 and p63 and their isoforms;
vi) molecular platform for designing new peptido-mimetic drugs able to target and perturb p73 and/or p63 and their isoforms.

Yet, further objects of the present invention are methods employing molecules comprising peptides or aptamers thereof capable to bind both conformational and structural p53 mutants or their isoforms, within the region corresponding to the wild-type p53 DNA binding core domain comprised from amino acids 74 to amino acids 298 sequence for:
vii) detection of p53 mutants in isolated cells or tissues;
vii) selection of biologically active peptido-mimetic compounds capable to specifically target tumor cells expressing mut-p53;
xi) selection of biologically active peptido-mimetic compounds capable to target and modulate p73, p63 and their isoforms and the peptido-mimetic compounds selected with the aforementioned methods as defined in the appended claims.

(a) Schematic representation of the pJG4-5-HA-TNV yeast two hybrid vector and of the pLPC-EGFP-TNV mammalian expression vector. These constructs express the TNV cassette, formed by the TRX (Thioredoxin A) cDNA, NLS nuclear localization signal and VSV tag. Oligonucleotides from a combinatorial library encoding 16mers peptide aptamers (PAs) were inserted at the RsrII restriction site in the TRX sequence. B42: transactivation domain. (b) Interaction of EGFP-TNV-PAs with p53R175H was analyzed by co-immunoprecipitation upon expression in H1299 cells. Following immunoprecipitation (IP) with anti-GFP antibody, immunoprecipitated proteins and input cell lysates were analyzed by Western Blot with the indicated antibodies. Cells transfected with p53R175H and pLPC-EGFP-TNV (−) were used as control.

Figure 2:
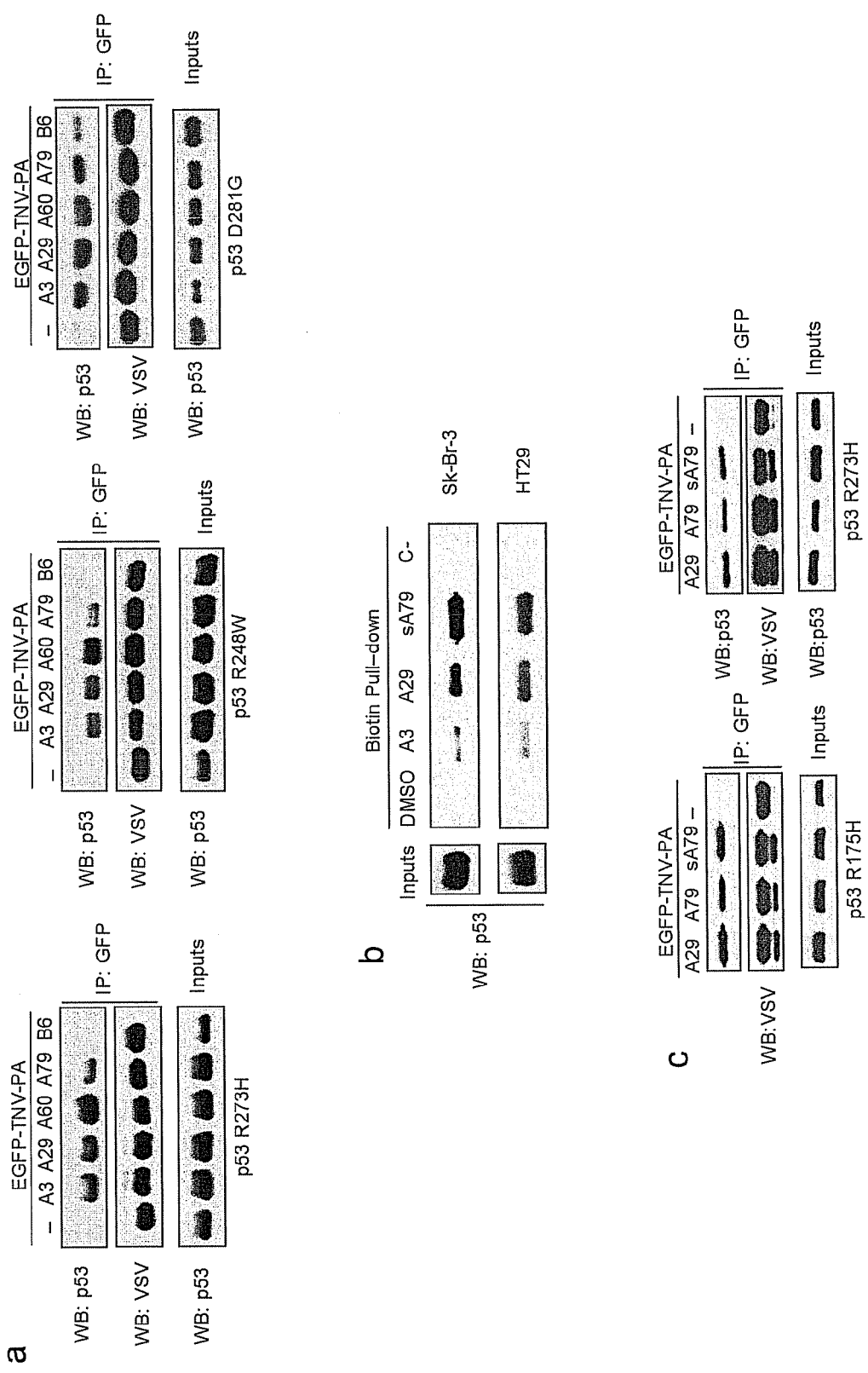
Figure 2:
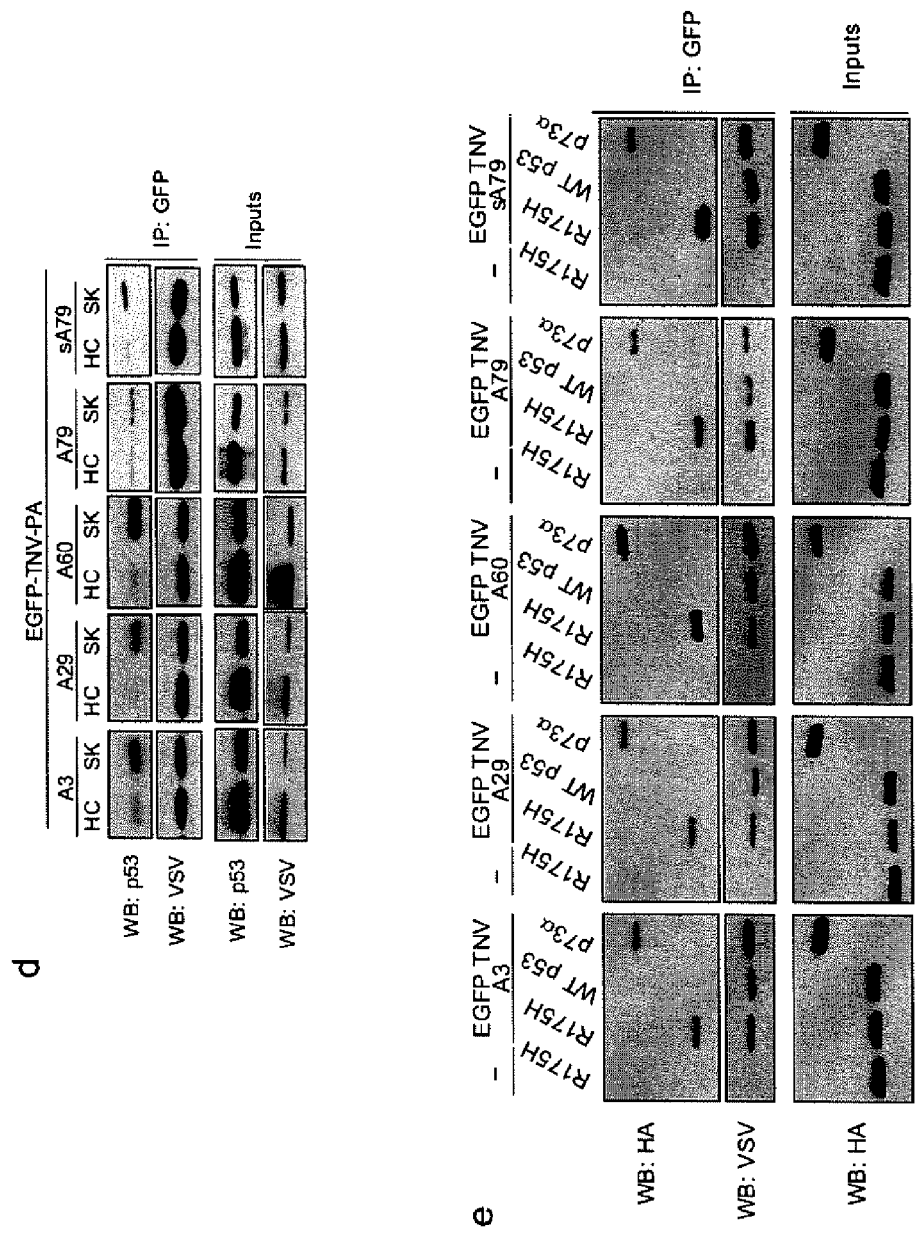

FIG. 2. Binding of PAs and Biot-16mers to mutant p53, wt p53 and p73.

Figure 1:
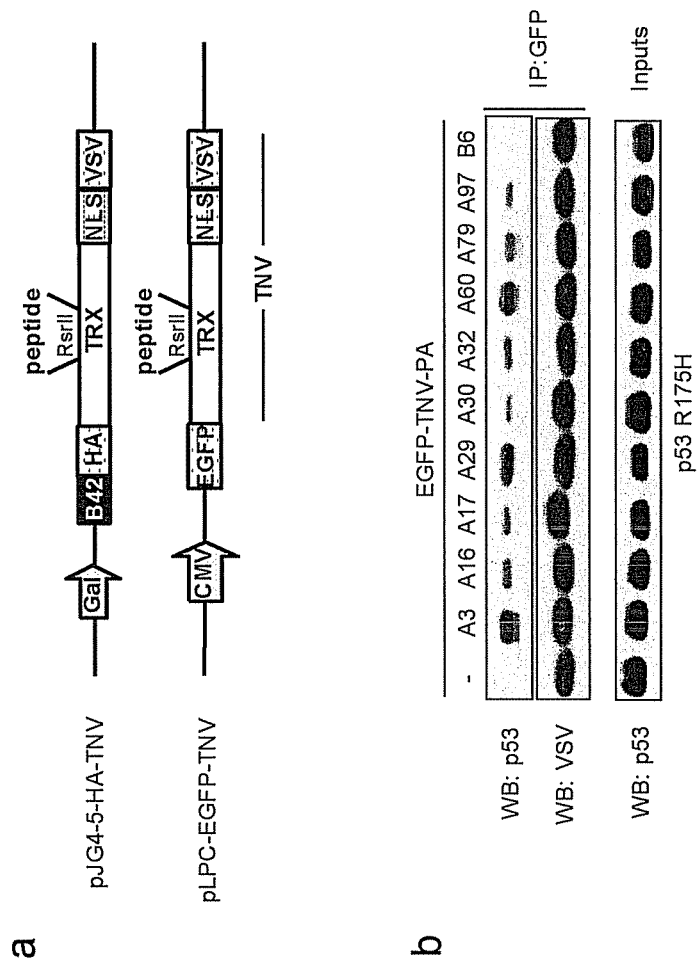
FIG. 1. Identification of peptide aptamers (PAs) interacting with mutant p53.

(a) The binding of EGFP-TNV-PAs with p53 mutants in H1299 cells was analyzed by co-immunoprecipitation upon transient transfection of PAs along with p53R273H (left), p53R248W (middle) or p53 D281G (right). Immunoprecipitations and Western Blot analysis were performed as in FIG. 1 (*b*). Cells transfected with the indicated mutant p53 and pLPC-EGFP-TNV (−) were used as control. (b) Binding of Biotin-16mers to mutant p53 in vitro was analyzed upon incubating cellular lysates of either Sk-Br-3 or HT-29 cells with Biotin-16mers. Streptavidin-affinity purified protein complexes, as well as 1% (5 µg) of total extracts as inputs, were then analyzed by Western Blot with anti-p53 antibody. (c) Analysis of EGFP-TNV-sA79 in vivo interaction with mutant p53R175H (left) or p53R273H (right) in H1299 cells as in FIG. 1(*b*). Co-Immunoprecipitations and Western Blot analysis were performed as in FIG. 1(*b*). (d) Analysis of the binding of EGFP-TNV-PAs with endogenous wild-type and mutant p53. HCT116 (HC) and Sk-Br-3 (SK) cells were transfected with EGFP-TNV-PAs and Co-IPs were then performed as in FIG. 1 (*b*). p53 wt in HCT116 cells was stabilized by an overnight treatment with Nutlin-3. (e) Comparison of the ability of EGFP-TNV-PAs to bind overexpressed HA-p53R175H, HA-wt p53 and HA-TAp73α in H1299 cells was performed as in FIG. 1(*b*). Cells transfected with HA-p53R175H and pLPCEGFP (−) were used as control.

Figure 3:
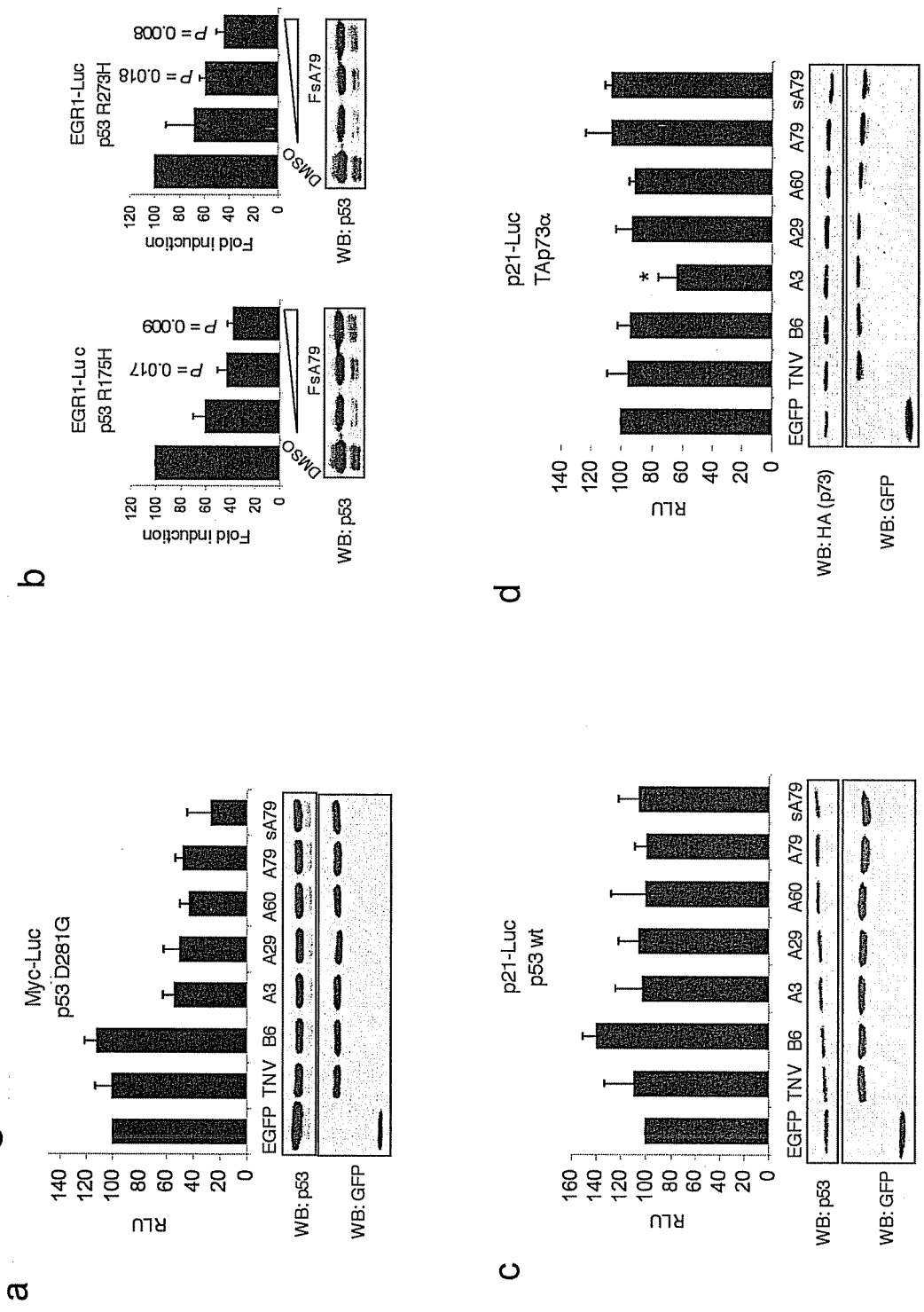
Figure 3:
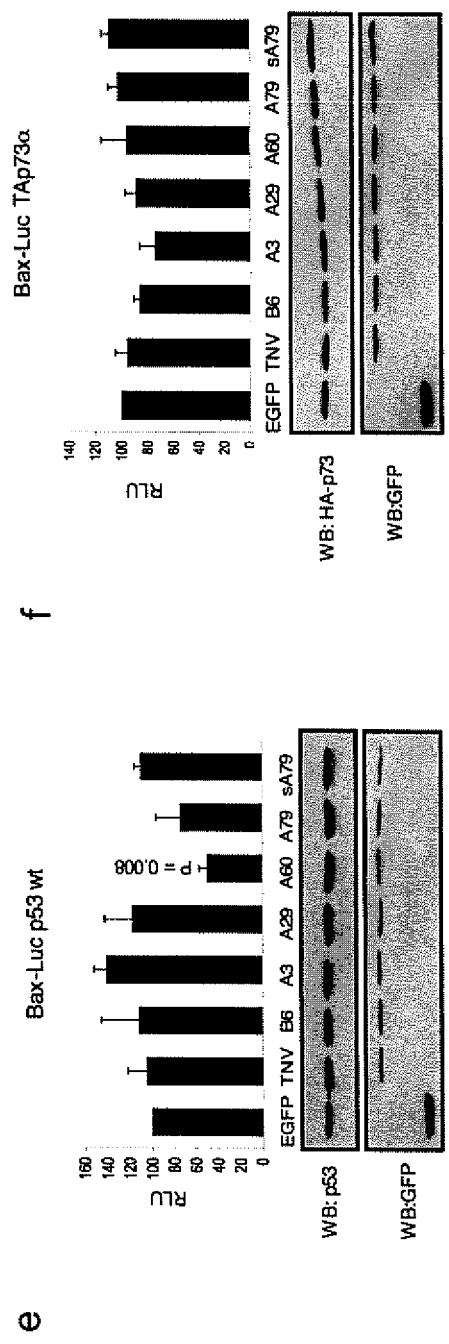

FIG. 3. Effect of PAs on the transcriptional activity of mutant p53, wt p53 and p73α

(a) The effect of PAs on mutant p53 transactivating activity was analyzed in MG63 cells transiently transfected with Myc-Luc reporter along with constructs expressing p53 D281G or empty vector and with pLPC-EGFP-TNV vectors expressing PAs or control vectors pLPC-EGFP (EGFP) or pLPC-EGFP-TNV (TNV). The promoter activity measured in each experiment was normalized to the value measured in the absence of mutant p53. RLU: Relative Luciferase Units. Graphs represent the means of three independent experiments, P value was <0.01 for all PAs relative to the aptamer B6, used as negative control, or pLPC-EGFP-TNV control vector. Expression of mutant p53 and PAs was analyzed by Western Blot with the indicated antibodies. (b) The effect of FsA79 peptide on the transactivation of EGR1 promoter by mutant p53 was analyzed in H1299 cells, transfected with EGR1-Luc reporter along with plasmids encoding either p53R175H (left) or p53R273H (right) and treated with increasing amounts of FsA79 peptide (1.6, 4, 20 µM). Luciferase assays were performed and represented as in (a). (c) The effect of PAs on p53 wt transcriptional activity was analyzed in H1299 cells transfected with p21-Luc reporter, wt p53-expressing vector or empty vector along with constructs expressing the EGFP-TNV-PAs or control vectors as in (a). Luciferase assays were performed and represented as in (a). (d) The effect of PAs on the transcriptional activity of TAp73α was analyzed as in (c). Asterisk means P value=0.003. (e) The effect of PAs on p53 wt transcriptional activity was analyzed in H1299 cells transfected with Bax-Luc reporter, wt-p53 expressing vector or empty vector together with constructs expressing EGFP-TNV-PAs or control vectors as in FIG. 3(c). Luciferase assays were performed and represented as in FIG. 3(c). An aliquot of each lysate was analized by Western Blot with the indicated antibodies. (f) Effect of PAs on TAp73a transcriptional activity on Bax-Luc reporter was analyzed as described in FIG. 3(d).

Figure 4:
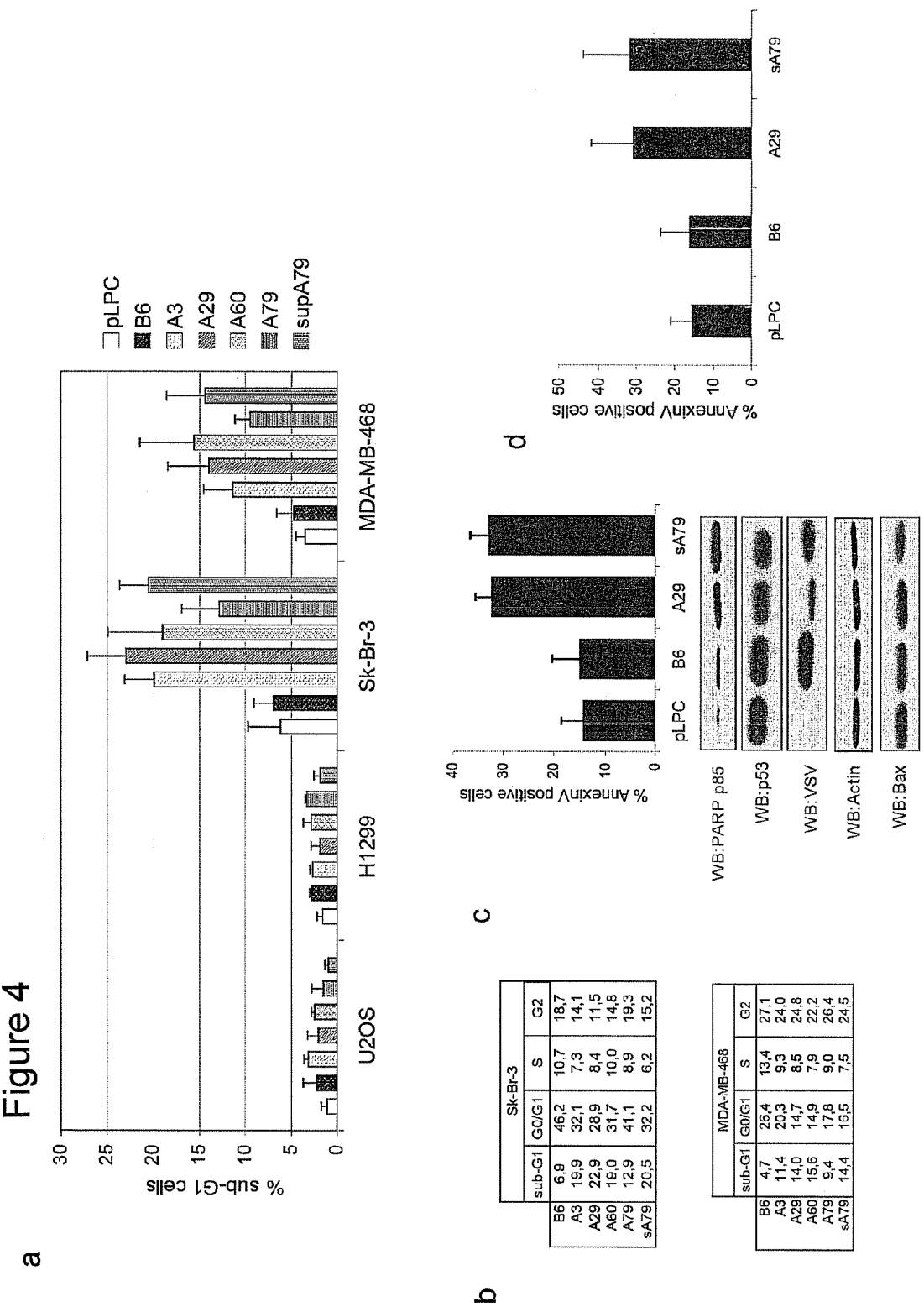
Figure 4:
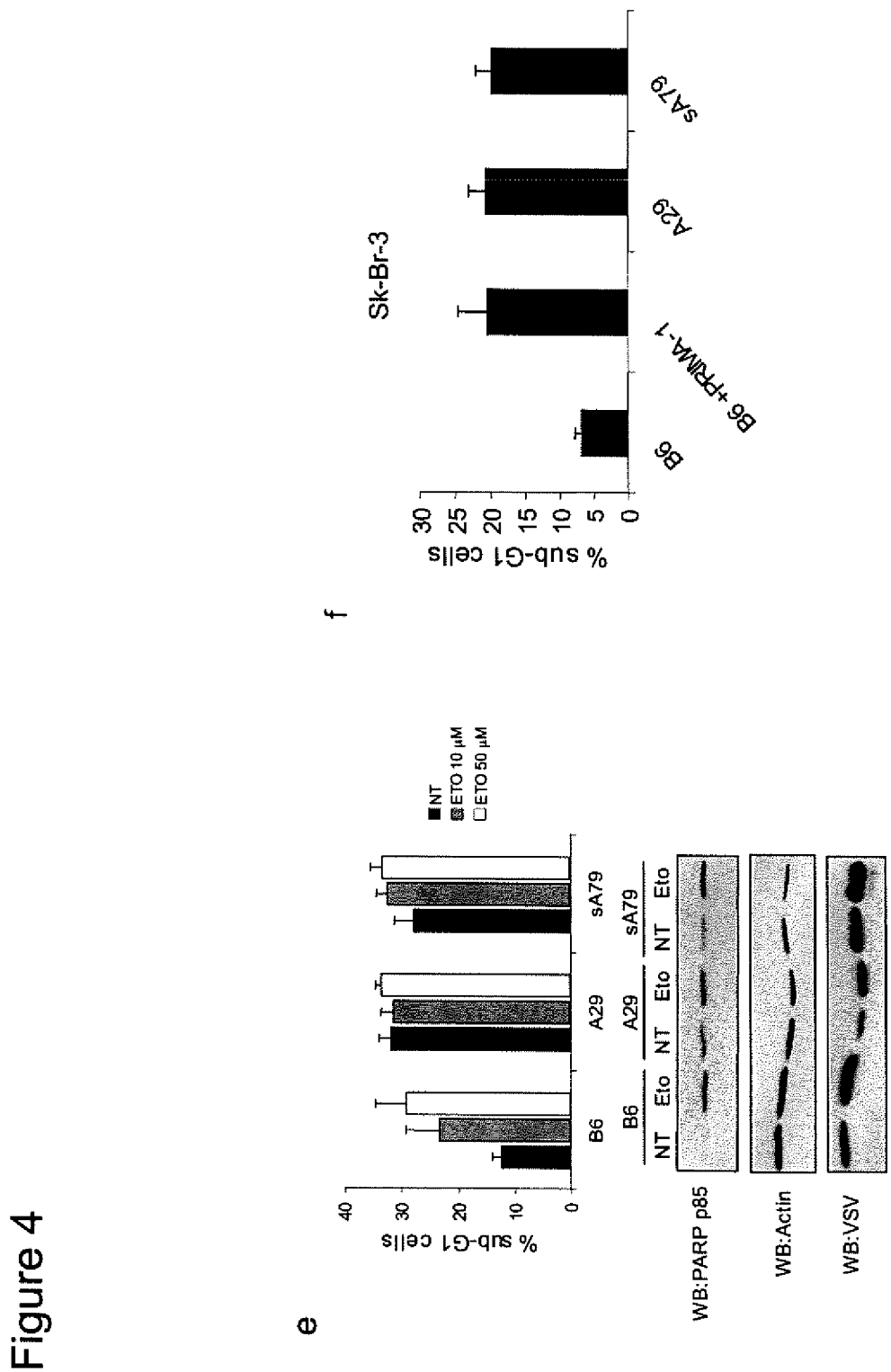

FIG. 4. Peptide aptamers trigger apoptosis specifically in cells bearing mutant p53.

(a) The apoptotic effect of PAs was analyzed in U20S (expressing p53 wt), H1299 (p53 null), Sk-Br-3 (expressing p53R175H) and MDA-MB-468 (expressing p53R273H) cells. Cells were transfected either with constructs expressing EGFP-TNV-PAs or with pLPCcontrol vector, harvested after 36 hours and stained with propidium iodide before analyzing the DNA content of EGFP-positive cells by flow cytometry. Histograms represent the average and the s.d. of the percentage of cells with sub-G1 DNA content measured in three independent experiments. The P values of individual PAs compared to negative controls (aptamer B6 or pLPC vector) were <0.01 in each cell line analyzed. (b) Tables representing cell cycle distribution of EGFP-positive Sk-Br-3 and MDA-MB-468 cells in one representative experiment of transient expression of EGFP-TNV-PAs in Sk-Br-3 described in FIG. 4(a). (c) Analysis of AnnexinV-PE-Cyan5 staining of Sk-Br-3 cells transfected with constructs encoding either EGFP-TNV-B6, -A29 or -sA79 PAs or with pLPC control vector. At least 10000 EGFP-positive cells were analyzed in each acquisition. Histograms represent the average and s.d. of three independent experiments. The P values of A29 and sA79 relative to B6 were <0.01. Expression of the overexpressed EGFP-TNV-PAs as well as endogenous cleaved PARP (p85), p53R175H and the proapoptotic protein Bax was analyzed by Western Blot with the indicated antibodies. (d) Analysis of AnnexinV-PE-Cyan5 binding of MDA-MB-468 cells treated and analyzed as described in FIG. 4(c). (e) Sk-Br-3 cells were transfected with constructs encoding EGFP-TNV-A29 and -sA79 PAs and then treated either with Etoposide 10 µM (grey bars), 50 µM (white bars) or with DMSO as control (NT, black bars). FACS analysis of DNA content was then performed as in (a). Aliquots of cell lysates untreated (NT) or treated with 50 µM Etoposide (Eto) were analyzed by Western Blot. (f) Comparison of the effect in Sk-Br-3 cells of transient overexpression of peptide aptamers A29, sA79 and B6 and treatment with PRIMA-1. Cells were transfected with EGFP-PAs and then left untreated or treated with 100 µM PRIMA-1. After additional 20 hours cells were harvested and analyzed as in FIG. 4(a).

DEFINITIONS

By wild-type p53 it is meant the protein having highly conserved sequences known for several animal species (from human to *C. elegans* and *D. melanogaster*). The human protein sequence corresponds to p53 protein [Homo sapiens] Accession ABB80262 393aa

```
                                              SEQ ID NO: 12
  1    MEEPQSDPSV EPPLSQETFS DLWKLLPENN VLSPLPSQAM
       DDLMLSPDDI EQWFTEDPGP

61    DEAPRMPEAA PRVAPAPAAP TPAAPAPAPS WPLSSSVPSQ
       KTYQGSYGFR LGFLHSGTAK

121    SVTCTYSPAL NKMFCQLAKT CPVQLWVDST PPPGTRVRAM
       AIYKQSQHMT EVVRRCPHHE

181    RCSDSDGLAP PQHLIRVEGN LRVEYLDDRN TFRHSVVVPY
       EPPEVGSDCT TIHYNYMCNS

241    SCMGGMNRRP ILTIITLEDS SGNLLGRNSF EVRVCACPGR
       DRRTEEENLR KKGEPHHELP

301    PGSTKRALPN NTSSSPQPKK KPLDGEYFTL QIRGRERFEM
       FRELNEALEL KDAQAGKEPG

361    GSRAHSSHLK SKKGQSTSRH KKLMFKTEGP DSD.
```

By TAp63a or p63 it is meant the wild-type protein having sequences known for several animal species. The human protein sequence corresponds to: TA p63 alpha [Homo sapiens] Accession AAG45607 680 aa

```
                                              SEQ ID NO: 13
  1    MNFETSRCAT LQYCPDPYIQ RFVETPAHFS WKESYYRSTM
       SQSTQTNEFL SPEVFQHIWD

61    FLEQPICSVQ PIDLNFVDEP SEDGATNKIE ISMDCIRMQD
       SDLSDPMWPQ YTNLGLLNSM

121    DQQIQNGSSS TSPYNTDHAQ NSVTAPSPYA QPSSTFDALS
       PSPAIPSNTD YPGPHSFDVS

181    FQQSSTAKSA TWTYSTELKK LYCQIAKTCP IQIKVMTPPP
       QGAVIRAMPV YKKAEHVTEV

241    VKRCPNHELS REFNEGQIAP PSHLIRVEGN SHAQYVEDPI
       TGRQSVLVPY EPPQVGTEFT

301    TVLYNFMCNS SCVGGMNRRP ILIIVTLETR DGQVLGRRCF
       EARICACPGR DRKADEDSIR

361    KQQVSDSTKN GDGTKRPFRQ NTHGIQMTSI KKRRSPDDEL
       LYLPVRGRET YEMLLKIKES

421    LELMQYLPQH TIETYRQQQQ QQHQHLLQKQ TSIQSPSSYG
       NSSPPLNKMN SMNKLPSVSQ

481    LINPQQRNAL TPTTIPDGMG ANIPMMGTHM PMAGDMNGLS
       PTQALPPPLS MPSTSHCTPP

541    PPYPTDCSIV SFLARLGCSS CLDYFTTQGL TTIYQIEHYS
       MDDLASLKIP EQFRHAIWKG

601    ILDHRQLHEF SSPSHLLRTP SSASTVSVGS SETRGERVID
       AVRFTLRQTI SFPPRDEWND

661    FNFDMDARRN KQQRIKEEGE.
```

By TAp73a or p73 it is meant the wild-type protein having sequences known for several animal species. The human protein sequence corresponds to: tumor protein p73 isoform a [Homo sapiens]
Accession NP 005418 636 aa

```
                                               SEQ ID NO: 14
  1    MAQSTATSPD GGTTFEHLWS SLEPDSTYFD LPQSSRGNNE
       VVGGTDSSMD VFHLEGMTTS

61    VMAQFNLLSS TMDQMSSRAA SASPYTPEHA ASVPTHSPYA
       QPSSTFDTMS PAPVIPSNTD

121    YPGPHHFEVT FQQSSTAKSA TWTYSPLLKK LYCQIAKTCP
       IQIKVSTPPP PGTAIRAMPV

181    YKKAEHVTDV VKRCPNHELG RDFNEGQSAP ASHLIRVEGN
       NLSQYVDDPV TGRQSVVVPY

241    EPPQVGTEFT TILYNFMCNS SCVGGMNRRP ILIIITLEMR
       DGQVLGRRSF EGRICACPGR

301    DRKADEDHYR EQQALNESSA KNGAASKRAF KQSPPAVPAL
       GAGVKKRRHG DEDTYYLQVR

361    GRENFEILMK LKESLELMEL VPQPLVDSYR QQQQLLQRPS
       HLQPPSYGPV LSPMNKVHGG

421    MNKLPSVNQL VGQPPPHSSA ATPNLGPVGP GMLNNHGHAV
       PANGEMSSSH SAQSMVSGSH

481    CTPPPPYHAD PSLVSFLTGL GCPNCIEYFT SQGLQSIYHL
       QNLTIEDLGA LKIPEQYRMT

541    IWRGLQDLKQ GHDYSTAQQL LRSSNAATIS IGGSGELQRQ
       RVMEAVHFRV RHTITIPNRG

601    GPGGGPDEWA DFGFDLPDCK ARKQPIKEEF TEAEIH.
```

By p53 R175H it is meant the conformational mutant protein in which arginine 175 present in wild-type p53 sequence is substituted by an histidine.

By p53 D281G it is meant the conformational mutant protein in which aspartic 281 present in wild-type p53 sequence is substituted by a glycine.

By p53 R273H it is meant the contact mutant protein in which arginine 273 present in wild-type p53 sequence is substituted by an histidine.

By p53 R248W it is meant the contact mutant protein in which arginine 248 present in wild-type p53 sequence is substituted by a tryptophan.

By isoform proteins of p53 it is meant the proteins generated by alternative splicing and/or alternative translational initiation of p53 mRNA identified by Bourdon and colleagues in 2005 (Bourdon, J. C., Fernandes, K., Murray-Zmijewski, F., Liu, G., Diot, A., Xirodimas, D. P., Saville, M. K. and Lane, D. P. p53 isoforms can regulate p53 transcriptional activity. *Genes & development*, 2005, 19:2122-2137).

Yet, by isoform proteins of p53 it is meant the proteins generated by alternative splicing and/or alternative translational initiation of p63 mRNA or p73 mRNA (reviewed in Murray-Zmijewski F. et al., 2006, ref. cit.).

By peptide aptamers it is meant a short variable length peptide, that can be expressed in the context of a scaffold protein, to interact strongly and specifically with its targets. Aptamers can be selected from high complexity libraries to specific target proteins and modulate their functions (Hoppe-Seyler, F., Crnkovic-Mertens, I., Tomai, E. & Butz, K. Peptide aptamers: specific inhibitors of protein function. *Curr. Mol. Med.*, 2004, 4:529-38).

By peptido-mimetic compounds or peptido-mimetics are meant compounds which are not necessarily petidic in nature but which mimic the biological activity of the peptide of the invention, while offering the advantages of increased bioavalability, biostability, bioefficiency and selectivity against the biological target of the parent peptide. Hence in the following description with peptido-mimetics are indicated compounds capable preferably to interact with contact and conformational mut-p53 or isoforms thereof within the region corresponding to wild-type p53 DNA binding core domain comprised from amino acids 94 to amino acids 298 sequence and more preferably further capable to interact and perturb p63 and/or p73 and isoforms thereof.

The terms "to bind" and "binding", "to interact" and "interaction(s)", "to complex" and "complex(es)" are to be considered synonymous, meaning in any case an interaction of the of the molecules of the invention with mut-p53 specific regions and/or with p63 and p73 able to induce a recognition of said proteins and/or a biological effect such as cell death in cells expressing mut-p53.

DETAILED DESCRIPTION OF THE INVENTION

Cancer is a complex disease that may be originated from several different alterations that interfere with normal cell behaviour. Considering the variability in the causative events that lead to tumor development, therapies should act in a very selective way, focalizing on the particular genetic alterations present in different tumor types, and on their consequences on cell physiology. Ideally, an efficient therapy should target exclusively tumor cells, without affecting adjacent normal cells. Accordingly, therapies based on inactivation of tumor-specific targets could optimize the selectivity and efficiency of cancer cell killing. Mutation of the p53 gene is one of the most frequent alterations in human cancer. The vast majority of cases consist on missense mutations leading to the expression of point mutants, which accumulate to high levels in tumor tissues. In this respect p53 mutants may be regarded as excellent markers of tumor cells.

The presence of p53 point mutants in tumor cells actively contributes to tumorigenesis, either by inhibiting wild-type p53 function or by acquisition of new functions as a consequence of mutation. Taking into account that in cells where the p53 gene is mutated the remaining wild-type allele is often deleted, a therapy designed to inhibit mutant p53 pro-oncogenic functions would help to hamper tumor progression, and would be highly selective, affecting only tumor cells.

Theoretically this purpose may be achieved acting on one of the different mechanisms previously reported by which the p53 mutants induce tumorigenesis.

In one possible way the suppression of pro-oncogenic functions of mut-p53 could be obtain both with peptides and peptide aptamers able to selectively bind p53 mutants, even though the complexity of the interactions of p53 mutants could hamper the expected effects.

Typically, the peptide aptamers consist of a short variable peptide domain presented in the context of a supporting protein scaffold (Hoppe-Seyler, F. et al. 2004, ref.cit.). A number of important properties represent the advantages of PAs in molecular medicine, both for therapy and diagnosis: first of all, high affinity for their targets (Colas, P., Cohen, B., Ko Ferrigno, P., Silver, P. A. & Brent, R. Targeted modification and transportation of cellular proteins. *Proc. Natl. Acad. Sci. USA*, 2000, 97:13720-5), high specificity, both in vitro and in vivo, and capability to specifically block the function of their target proteins in vitro, as well as in living cells, and even in whole animals (Hoppe-Seyler, F. et al. 2004, ref.cit.).

In order to identify new peptides or peptide aptamers interactors, a selection from a combinatorial expression library by a screening system based on the yeast two-hybrid technology (Colas, P, Cohen B, Jessen T, Grishina I, McCoy J, Brent R. Genetic selection of peptide aptamers that recognize and inhibit cyclin-dependent kinase 2, *Nature*. 1996, 380 (6574): 548-50) can be used. Therefore, this technology was applied by the inventors for the selection of new peptides or peptides aptamers presumably suitable to interact with contact and conformational p53 mutants and isoforms thereof in the region corresponding to wild-type p53 DNA binding core domain comprised from amino acids 94 to amino acids 298 sequence.

From this selection the inventors have identified ten peptides and aptamers of the same, namely A3, A29, A60, A79, A16, A17, A30, A32, A97, B6, and an eleventh coded as sA79 has derived from the A79, having the sequences:

| | |
|---|---|
| AKYCQCAAKVRVTAAM (A3) | Seq ID No 1 |
| GPVVPRTQYMSLAFGW (A29) | Seq ID No 2 |
| IQITLTGWSARVTTSG (A60) | Seq ID No 3 |
| VWAESCDDCGEYWRYV (A79) | Seq ID No 4 |
| DVADWESCGEYWCYRV (sA79) | Seq ID No 5 |
| QAGSGREKCQHAAYLS (A16) | Seq ID No 6 |
| ARTDTAVVHVCDSGRQ (A17) | Seq ID No 7 |
| QQSRGRCPSCIPEAAS (A30) | Seq ID No 8 |
| PGKLIRVSENMSSALG (A32) | Seq ID No 9 |
| TPEGLDVALAVAAYSV (A97) | Seq ID No 10 |
| QRGLYCSCVTNQNAEV (B6) | Seq ID No 11 |

The selected peptides are similar there between both for their molecular weight being formed all by 16 amino acids (aa) and with respect to the global charge (the majority of them consist of basic and hydrophobic aa with the exception of aptamers Seq. ID No 4, 5, 10 which have a pI lower then 4.

In detail the following are the primary sequence analysis performed by the ProtParam tool:

Peptide Seq. ID No 1:
AKYCQCAAKVRVTAAM (A3), MW=1714.0, theorethical pI=9.39. As regards for its aa composition it is formed by 3 positively charged residues (aa R, K), 10 hydrophobic residues (aa A, C, V, M) and 2 neutral residues (aa T, Y).

Peptide Seq. ID No 2:
GPVVPRTQYMSLAFGW (A29), MW=1809.1, theorethical pI=8.75. It is formed by 1 positively charged residue (aa R), 8 hydrophobic residues (aa A, V, M, F, W) and 6 neutral residue (aa Y, T, S, G, P).

Peptide Seq. ID No 3:
IQITLTGWSARVTTSG (A60), MW=1690.9, theorethical pI=9.75. It is formed by 1 positively charged residue (aa R), 6 hydrophobic residues (aa A, V, I, L, W) and 8 neutral residue (aa T, S, G).

Peptide Seq. ID No 4:
VWAESCDDCGEYWRYV (A79) and Peptide Seq. ID No 5: DVADWESCGEYWCYRV (sA79), MW=1981.1, theorethical pI=3.92. They are formed by 1 positively charged residue (aa R), 7 hydrophobic residues (aa A, V, C, W) and 4 neutral residue (aa Y, S, G). In contrast to the previous peptide sequences, these contain also 4 negatively charged residues (aa D, E).

Peptide Seq. ID No 6:
QAGSGREKCQHAAYLS (A16), MW=1705.8, theorethical pI=8.21. It is formed by 2 positively charged residue (aa R, K), 6 hydrophobic residues (aa A, V, I, L, W) and 8 neutral residue (aa T, S, G).

Peptide Seq. ID No 7:
ARTDTAVVHVCDSGRQ (A17), MW=1714.8, theorethical pI=6.78. It is formed by 2 positively charged residue (aa R), 6 hydrophobic residues (aa A, V, C), 5 neutral residue (aa H, T, S, G) and 2 negatively charged residues (aa D).

Peptide Seq. ID No 8:
QQSRGRCPSCIPEAAS (A30), MW=1689.8, theorethical pI=8.07. It is formed by 2 positively charged residue (aa R), 5 hydrophobic residues (aa I, A, C), 6 neutral residue (aa P, S, G) and 1 negatively charged residues (aa E).

Peptide Seq. ID No 9:
PGKLIRVSENMSSALG (A32), MW=1658.9, theorethical pI=9.18. It is formed by 2 positively charged residue (aa R, K), 6 hydrophobic residues (aa I, A, L, M, V), 6 neutral residue (aa P, S, G) and 1 negatively charged residues (aa E).

Peptide Seq. ID No 10:
TPEGLDVALAVAAYSV (A97), MW=1575.7, theorethical pI=3.67. It is formed by 9 hydrophobic residues (aa A, L, V), 5 neutral residue (aa Y, T, P, S, G) and 2 negatively charged residues (aa D, E). It does not contain any positively charged residue (aa R, K).

Peptide Seq. ID No 11:
QRGLYCSCVTNQNAEV (B6), MW=1784.9, theorethical pI=5.99. It is formed by 1 positively charged residue (aa R), 6 hydrophobic residues (aa A, L, V, C), 4 neutral residue (aa Y, T, S, G) and 1 negatively charged residue (aa E).

Taking advantage of the restricted degrees of freedom of the PAs conformation when inserted in the thioredoxin scaffold, the inventors have modelled the conformation of PAs through in silico analysis. Despite the lack of significant homology among their sequences, the backbones of PAs appeared to share a fairly similar extended conformation in their N-terminal part.

For the docking of PAs onto mutant p53, the inventors used the X-ray structure of superstable p53R273H, which contains four stabilizing mutations (M133L, V203A, N239Y and N268D) (PDB CODE: 2BIM) (Joerger, A. C., Allen, M. D., and Fersht, A. R. Crystal structure of a superstable mutant of human p53 core domain. Insights into the mechanism of rescuing oncogenic mutations. *J. Biol. Chem.*, 2004, 279; 1291-1296.). At present this is the only crystal structure available for mutant p53. Indeed, despite the good knowledge of the structure of the wt p53 core domain, there are only few structural information about the core domains of p53 mutants, due to their high thermodynamic instability. In the docking analysis, all the stabilizing mutations have been reversed using Swiss-Pdb Viewer program. Two regions of p53 R273H were predicted to be important for docking of all the PAs considered (for details see Table 2 hereinafter reported). They involve the N-terminus of CD (comprised from aa 94 to aa 298) and the loop-sheet-helix (LSH) motif (including aa 124 to 135 and 264 to 286), which establish a large number of polar interactions with the aptamers, particularly Thr102, Leu130 and Asn131 that interact with four out of five PAs (or details see Table 2 hereinafter reported). A29 and sA79 also form extensive hydrophobic interactions with Leu11, Phe113, Tyr126, Pro128 and Thr102, Tyr103, respectively. Other residues predicted to be contacted by some aptamers comprise Leu111-His115 (L1), Tyr126-Lys132 (S2/S2'), and Lys164-His273 (L2-H1).

From this set of peptides and aptamers thereof the inventors have selected 5 of them as the strongest interactors with mut-p53, while the peptide aptamer B6 (Seq. ID No 11) that did not show any interaction with mut-p53. These are peptides named Seq. ID No 1-5, which are able to recognize selectively p53 structural and conformational mutants, but not wild-type p53.

The selected 5 peptides and aptamers thereof of the present invention, properly expressed in cells, interfere specifically with mutant p53-associated functions and trigger apoptosis only in tumor cells bearing mutant p53.

In fact, the identified peptides and aptamers thereof, with the exception of B6 of Seq. ID No 11, bind conformational mutants, such as p53 R175H or D281G, and contact mutants, such as p53 R273H and p53 R248W, conversely, they display a greatly reduced affinity for wild-type p53, suggesting that they may recognize a structural motif present in all tested mutants, but absent in the wild-type conformation. Moreover aptamers bind mutant p53 also as unconstrained peptides without the thioredoxin scaffold. In addition to this capability the selected peptides or aptamers thereof complex also other members of the p53 proteins family, such as p63 and p73. Regarding the ability to selectively recognize and bind mutant p53, PAs behave like antibodies able to discriminate between folded or denatured p53, such as PAb 240 or 1620 (Joerger, A. C. and Ferht, A. R., 2007, ref. cit.). Even if there is no sequence similarity between the identified PAs, modelling the interaction by docking analysis predicted that all of them would bind the same region of the protein, suggesting that this region may be favoured for the interaction with different partners.

According to the results obtained the interaction between PAs and mutant p53 can interfere with some of its functions. The observation that PAs reduce the ability of p53 mutants to transactivate target promoters indicates that the functional performance of p53 mutants may be affected. According to their reduced affinity for wild-type p53, PAs did not affect its ability to induce p21 promoter. Interestingly, even if PAs interact with TAp73α, they do not affect its transactivation activity.

A strong increase in cell death upon expression of PAs of the present invention in different cells lines bearing endogenous mutant p53 has observed. In contrast, the same PAs transfected in cells expressing wild-type p53 or in p53-null cells did not produce any effect, suggesting that induction of apoptosis depends on the presence of mutant p53. The ability of peptides or small molecules to induce mutant p53-dependent apoptosis was previously reported (Selivanova, G., Wiman, K. G. ref. cit.) as well as ablation of mutant p53 was already associated with an increment in cell death upon treatment with genotoxic drugs (Bossi, G., et al., 2006, ref. cit.). Expression of PAs of the present invention alone, however, induced an apoptotic response similar to that induced by etoposide or cisplatin, or to that exerted by PRIMA-1, suggesting that its association with mutant p53 may have a cytotoxic effect. Even if the mechanism by which PAs induce apoptosis is unknown, it is conceivable that they may interfere with functions of mutant p53 associated with survival. PAs of the present invention do not restore transactivation of wild-type p53 targets, but they could induce in p53 mutants the ability to trigger transcription-independent pro-apoptotic functions. Alternatively, PAs could interfere with the ability of mutant p53 to block an apoptotic response. Considering that the PAs provided by the present invention engage in a physical interaction with mutant p53, they could alter its ability to interact with different partners either by modifying p53 structure or by directly displacing other interactors.

It is conceivable that PAs-induced apoptosis may arise from the activation of both classic apoptotic pathways as well as alternative types cell death. Indeed, recently it was reported that a C-terminal peptide of p53 (p53p-Ant) could induce multiple mechanisms of death depending on the cell type treated (Dinnen, R. D., Drew, L., Petrylak, D. P., Mao, Y., Cassai, N., Szmulewicz, J., Brandt-Rauf, P., Fine, R. L. Activation of targeted necrosis by a p53 peptide: a novel death pathway that circumvents apoptotic resistance. *J. Biol. Chem.*, 2007, 282(37):26675-86).

Considering the results in a broader perspective, the peptides or PAs of the present invention can be used as readily apparent to one skilled in the art as inhibitors of mut-p53-associated pro-oncogenic functions in cancer therapy as well as they may represent a starting point to design peptidomimetic drugs able to specifically target tumor cells. Moreover, the ability of PAs to specifically interact with mutant p53 could make the same useful as reagents for analysis of the expression of p53 mutants or to design reagents for the same purpose. The availability of such reagents would represent a greater improvement for detection of mutant p53 since specific antibodies useful for immunohistochemistry are lacking. Alternatively, peptides or PAs could also be used as carriers for molecular targeting of antitumoral compound. As example the PAs can be fused to the catalytic domain of ubiquitin ligases in order to specifically target mutant p53 for proteolytic degradation by the ubiquitin system, as already done for other aptamers and their target proteins (Colas, P. et al. 2000, ref. cit.). Moreover the peptides synthesized in fusion with so-called penetrating peptides can be used directly on cells (Kabouridis, P. S. Biological applications of protein transduction technology. *Trends in Biotech.*, 2003, 21:498-503).

Therefore, according to an embodiment, the present invention relates to molecules comprising peptides or aptamers thereof that are capable to bind contact and conformational p53 mutants and isoforms thereof within the region corresponding to wild-type p53 DNA binding core domain comprised from amino acids 74 to amino acids 298 sequence. Preferably said peptides and aptamers are able to interact with one or more amino acids by polar or hydrophobic interactions with one or more sub-domains of said region comprised from amino acid 100 to amino acid 135, and in this sub-domain particular from aa 100 to aa 115, and from aa 124 to aa 135, and from the amino acid 164 to amino acid 273.

In addition to this capability the peptides or aptamers thereof according to the invention are also capable to complex other members of the p53 family proteins, namely p63 and p73 and their isoforms.

The molecules according to the invention are in a preferred aspect peptides or aptamers thereof or polypeptides comprising said peptides or aptamers, said peptides or polypeptides can also be further chemically modified.

In particular, according to a preferred aspect said peptides and aptamers thereof comprise peptides having the Seq. ID No 1-10 and more preferably comprise peptide having the Seq. ID No 1-5. In a particularly preferred aspect the peptide comprises the Seq. ID No 5.

Furthermore said peptides and/or aptamers thereof can be modified according to known methodology so that they can be stabilized against the degradation of proteases or can be compartmentalize or localize into the target tissues and/or cells expressing mutant p53. For the purpose to enhance their stability the peptides and/or the aptamers thereof can comprise further amino acidic sequences at C- or N-terminals or chemical or biochemical modifications, such as for example myristoylation, amidation, biotynilation and glycosilation, which do not change their biological activity.

The peptides and the aptamers thereof of the invention can be prepared by known methodology, such as recombinant technology using nucleotide sequences encoding peptide and aptamers thereof as above defined, in particular the nucleotide sequences encoding peptide having the Seq. ID No 1-10 and the aptamers of the same peptides constrained in scaffolds selected from E. coli thioredoxin A or others, such as human stefin A (Woodman, R., Yeh, J. T., Laurenson, S., and Ko Ferrigno, P. Design and validation of a neutral protein scaffold for the presentation of peptide aptamers. J. Mol. Biol., 2005, 352:1118-1133).

The peptides can be also prepared by chemical synthesis and in this case they may comprise chemically modified amino acids and/or uncommon and/or non-natural amino acids in D- or L-configuration suitable to stabilize said peptides to proteases.

For the purpose to target the peptides to cells expressing mut-p53, they can also be prepared by chemical synthesis or recombinant technologies in fusion with penetrating peptides. These penetrating peptides have a streach of basic amino acids identified for example in D. melanogaster antennapedia homeoprotein (Antp) and in the human immunodeficient virus (HIV)-1 Tat that promote the delivery of peptides and proteins fused to them into cells (Kabouridis P. S. ref. cit.). Therefore the invention refers also to nucleic acid sequence encoding the above peptides either alone or in association with the nucleic acid sequence encoding for a protein scaffold or fusion penetrating peptides. Typically, said nucleic acids are cloned in a vector, to allow expression of the aptamer in a protein scaffold or in fusion with penetrating peptides by recombinant means. Suitable scaffolds are E. coli thioredoxin A, human stefin A, while fusion penetrating peptides can be derived from the established domains described in the D. melanogaster antennapedia homeoprotein (Antp) or in the human immunodeficient virus (HIV)-1 Tat (Kabouridis P. S. ref. cit.).

The capability of the peptides and aptamers according to invention to bind the contact and conformational p53 mutants and isoforms thereof within the region corresponding to wild-type p53 DNA binding core and related sub-domains can be measured by in vitro binding assay with cellular extracts from Sk-Br-3 cells or HT-29 cells, expressing endogenous p53 R175H and R273H respectively or in a adapted ELISA (Enzyme-Linked ImmunoSorbent Assay) or in peptide-aptamer microaarays (Evans D, Johnson S, Laurenson S., Davies A G, Ko Ferrigno P, and Walti C. Electrical protein detection in cell lysates using high-density peptide-aptamer microarrays. J. Biol., 2008, 7:3). These methods can be used also for selection of peptido-mimetic compounds able to mimic the biological activity of the molecules comprising the peptides and aptamers thereof of the present invention.

Therefore, the invention extends to the use of the peptides and aptamers thereof as inhibitors of mutant p53-associated pro-oncogenic functions in cancer therapy and to pharmaceutical compositions comprising at least one of the molecules comprising the peptides or aptamers thereof of the invention as active principle in combination with pharmaceutically acceptable excipients, diluents and/or delivery systems of the active principle. Said compositions can be formulated both for systemic and local administration.

Due to their affinity with both conformational and structural p53 mutants, the molecules comprising peptides or aptamers thereof of the invention can be also useful in delivering at the molecular target mut-p53 oncosuppressor compounds so that the use of the same as carrier of antitumoral drugs is part of the invention. Yet, it is another embodiment of the present invention the preparation of an antitumoral drug, wherein the active principle is at least one molecule comprising a peptide or an aptamer according to the invention, and wherein the peptides have preferably the Seq. ID No 1-10, more preferably Seq. ID No 1-5.

As far as the use of the peptides and aptamers thereof according to the invention for detection of conformational or structural p53 mutants is concerned, this can be directed to research or diagnostic purposes and then they can be used mainly as reagents.

In the case of diagnostic use the assay can be carried out in vivo administering properly labelled peptide and/or the aptamers and/or in vitro in isolated tumoral cells or tissues. In this latter case the petides and/or the aptamers thereof can be included as a reagent in kits prepared as known to one skilled in the art.

Yet, the peptides and/or the aptamers thereof according to the invention can be also employed as template to design new peptidomimetic compounds potentially acting as inhibitors of mut-p53 pro-oncogenic functions and/or further interacting with p63 and/or p73 and isoforms thereof.

Therefore, also this utilization of said peptides and aptamers thereof is part of the invention.

Accordingly, are further embodiments of the invention the methods for detection of mut-p53 as well as for selection of said new peptidomimetic compounds having an inhibitory activity for mut-p53 function and/or being able to complex p63 and/or p73.

Hence, also the peptido-mimetics selected with the selection method aforementioned are part of the present invention. These peptido-mimetic compounds can be molecules that are no longer completely or partially peptidic in nature but conserve the structural features of the parent peptide(s) of which mimic the biological activity. As known to one skilled in the art, they can be pseudo-peptides, semi-peptides and peptoids, but in any case they provide the structural requirement of the parent peptides for the interaction with contact and conformational mut-p53 or isoforms thereof within the region corresponding to wild-type p53 DNA binding core domain comprised from amino acids 74 to amino acids 298 sequence and/or for the interaction with p63 and p73 and isoforms thereof.

In particular, said petido-mimetics can comprise one or more amino acids which interact by polar or hydrophobic interactions with one or more of p53 sub-domains of the DNA binding core domain region, said sub-domains comprised within residues corresponding to aa 100-135 and aa 160-273 of wild-type p53 sequence. These peptido-mimetics can be useful because their increased bioavalability, stability and selectivity for the molecular target respect to parent peptides.

Experimental Part

Methods

Combinatorial Library Construction, Yeast Two Hybrid Screening and Plasmids

Vectors used in the Yeast two hybrid screening were pLexAp53R175H74-298, pLexAp53R175H74-393 and pLexAp5374-393, which express the baits and pJG4-5-HA-TNV16mers, which expresses the preys library. The high complexity peptide library was constructed by cloning a mixture of degenerated oligonucleotides into the RsrII restriction site, present inside the sequence corresponding to the catalytic region of E. coli Thioredoxin (TrxA). Oligos contain 16 repetitions of the codon NNG/T (N=any nucleotide) flanked by two regions with defined sequences comprising the site for a restriction enzyme compatible with RsrII. This construct mediates the expression of the preys, inserted in the TrxA sequence, as fused to the sequence of the transactivation domain of E. coli B42 and the expression of such proteins are under the transcriptional control of the inducible promoter Gal1.

The genetically engineered yeast strain S. cerevisiae, EGY48 (MATa trp1 ura3 h is 3 LEU2::pLEXAop6LEU2) was used. The yeast strain EGY48/pSH18-34/p53R175H74-298 was initially transformed with the library construct pJG4-5-HA-TNV16mers for the primary screening. About 9 million of clones were plated in selective media and 53 positive clones were confirmed by a secondary screening, according the classical procedure of Yeast two Hybrid System (Colas, P. et al., 1996, ref. cit.). Expression vectors for mutant p53 (pcDNA3-p53R175H or R273H or R248W) and pcDNA3-HAp63α were already present in the lab. p53D281G vector and c-MycD1 reporter were obtained from G. Zambetti. EGR1 luciferase reporter was kindly provided by V. Rotter. pcDNA3-HAp73α has been kindly provided by G. Melino. pLPCEGFP-TNV presents downstream the EGFP sequence, the TNV expression cassette, subcloned from pJG4-5TNV16mers library vectors, as EcoRI-XhoI digested fragments.

Peptides

Peptides corresponding to the sequences of A3, A29, A79, sA79, B6 and C– were synthetized on solid phase (Fmoc/t-Bu chemistry) at ICGEB (International Centre for Genetic Engineering and Biotechnology), Trieste, Italy. The synthesis was automatically performed on a 0.05 mM scale with a Gilson Aspec XI Solid Phase Extraction instrument modified in-house. After cleavage from the resin the peptides were precipitated, washed with diethylether and freeze-dried. The peptides were purified by RP-HPLC on a Zorbax 300SB-C18 column (Agilent) using a linear gradient from Eluent A (0.1% trifluoroacetic acid in water) to Eluent B (0.1% trifluoroacetic acid in acetonitrile). The collected fractions were analyzed by LC-MS using a API150EX single quadrupole mass spectrometer (Applied Biosystems), pooled and freeze-dried. Table 1 shows the peptide respective aa sequences. Peptide A60 was not synthetized due to technical problems.

TABLE 1

Peptide amino acid sequences

| PA Name | Sequence |
| --- | --- |
| A3 | AKYCQCAAKVRVTAAM |
| A29 | GPVVPRTQYMSLAFGW |
| A60 | IQITLTGWSARVTTSG |
| A79 | VWAESCDDCGEYWRYV |
| sA79 | DVADWESCGEYWCYRV |
| A16 | QAGSGREKCQHAAYLS |
| A17 | ARTDTAVVHVCDSGRQ |
| A30 | QQSRGRCPSCIPEAAS |

TABLE 1-continued

Peptide amino acid sequences

| PA Name | Sequence |
| --- | --- |
| A32 | PGKLIRVSENMSSALG |
| A97 | TPEGLDVALAVAAYSV |
| B6 | QRGLYCSCVTNQNAEV |
| C– | SFDTDVLKADGAILVD |

The peptides were HPLC purified to more than 95% pure. Peptide stocks (4 mM) were prepared in DMSO and stored in aliquots at −20° C.

C– is a peptide derived from the sequence of Thioredoxin and is used as control.

Modelling and Docking Analysis

The structure of mutant p53 R273H was built from the crystal structure (PDB entry: 2BIM) after reversing all the mutations that were necessary for crystallization (M133L, V293A, N239Y and N268D) by means of the Swiss-PDB Viewer program. Aptamers were first modelled as loops inserted inside thioredoxin NMR structure (PDB entry: 1XOB) by means of Modeler8v2 program. The central structures of the best five clusters of each peptide were chosen as representative of the peptide structure. Peptides underwent to blind docking against mutant p53 by using the AutoDock 3.0.5 program which considers the protein static. Regarding the ligand only side chains were considered flexible, as partial backbone conformational variability is considered by docking the five most representative structures of each peptide. Eventually, 1,250 different complexes of each peptide were produced.

Cell Culture, Transfections and Immunofluorescence Assays

H1299, Sk-Br-3, HCT116, MG63, HT-29, and MDA-MB-468 cells were cultured following standard procedures. Transfections of all cell lines were performed with Lipofectamine 2000 (Invitrogen) according to the manufacturer instructions.

For luciferase assays, H1299 cells were seeded in 24-wells plates and transfected with 250 ng of EGR1Luc reporter, 600 ng of p53R175H or R273H expression plasmids and 20 ng of the reporter pRL-CMV (Promega). FAM-Ahx-peptide sA79 (FsA79) (1 μl DMSO 500× stock/trasfection) were added at the cDNA premix. Alternatively, MG63 were seeded in 24-wells plates and transfected with 600 ng of c-MycD1Luc reporter, 250 ng of p53D281G expression plasmids, 20 ng of the reporter pRL-CMV (Promega), together with one pLPCEGFPTNV16mer or pLPCEGFP-TNV or pLPCGFP (500 ng). In both cases, 36 hours after transfections, cells were lysed and assayed for luciferase activity using the Dual Luciferase kit (Promega). Immunofluorescence analysis were performed on H1299 or Sk-Br-3 cells seeded on a coverslip and transfected with pLPCEGFPTNV16mers constructs or treated with FsA79 (final concentration 8 μM) and fixed with PFA 3%. After incubation with the indicated antibodies or WGA-TRITC (Sigma), cells were incubated with Hoecsht. Images were obtained with a Zeiss confocal microscopy.

In Vivo Co-immunoprecipitation, In Vitro Binding Assays and Western Blot Analysis HCT116 and Sk-Br-3 cells were transfected with the indicated vectors and further processed 24 hours later. HCT116 cells were treated with 8 μM Nutlin-3 for overnight before harvesting. Lysis of cells was performed in Mutant p53 CoIP buffer (150 mM NaCl, 50 mM Tris pH7.5, 0.5% NP40, 10% glycerol, 0.1% EDTA) supplemented with phosphatase inhibitors (NaF 1 mM, sodium beta-glycerol phosphate 1 mM and sodium orthovanadate 2 mM) and protease inhibitors (PMSF and CLAP). Lysates were then incubated with anti-GFP antibody previously cross-linked to Protein G-Sepharose CL-4B (Amersham Biosciences). Immunoprecipitated proteins were separated by SDS-PAGE and analysed by Western Blot with the indicated antibodies according to standard procedures.

For in vitro binding assays, cells were harvested in cold lysis buffer 300 (50 mM Tris-HCl pH 7.5, 300 mM NaCl, 10% glycerol, 0.5% Np-40, 1 mM EDTA, plus phosphatase and proteases inhibitors). Surnatant was collected and diluited to 150 mM NaCl. After preclearing with streptavidin-coated agarose beads (Sigma), protein concentration was determined by a colorimetric assay (Bio-Rad), 0.5 mg of lysate incubated with each biotin-16mer at final concentration of 10 mM for 2 hours at 4° C. and then streptavidin-coated agarose beads were added for 30 minutes. Retained material as well as 1% (5 μg) of total extract were resolved by SDS-12.5% PAGE. Western Blot analysis was performed using the following antibodies: polyclonal anti-GFP serum affinity purified; N-terminal human anti-p53 monoclonal antibody (clone: DO1, S.Cruz Biotechnology, CA); monoclonal anti-HA (SIGMA); monoclonal anti-VSV (SIGMA); anti-PARP cleaved p85 polyclonal antibody (Promega); horse-radish peroxidase conjugated secondary antibodies (SIGMA). Bound antibodies were visualised by enhanced chemiluminescence (Pierce).

FACS Analysis

Sk-Br-3, MDA-MB-468, H1299 or U20S cells were seeded in 6 wells and transfected with pLPCEGFP-TNV16mers or pLPCEGFP-TNV or pLPC. For cell cycle analysis, cells were collected by trypsinization, recovering also the supernatants, and resuspended in PBS/0.1% Nonidet P-40 (NP-40) containing 2 μg/ml RnaseA. 10 min later, 10 μg/ml propidium iodide was added. Cells were analyzed by cytofluorimeter (FACScalibur) after additional 20 minutes. At least 10000 EGFP-positive cells were analyzed in every acquisition. For AnnexinV binding analysis, 36 hours after transfection, 200000 cells were collected and washed as previous, then were resuspended in 1× Binding Buffer (#1035-100, BioVision) and AnnexinV-PE-Cyan5 reagent (#1015-200, BioVision) were added. After 5 minutes incubation, cells were analyzed for AnnexinV-PE-Cy5 binding by flow cytometer. Etoposide (SIGMA) was prepared in DMSO 50 mM Stock. PRIMA-1 was kindly provided by Klas Wiman.

Results

Isolation of Mutant p53-interacting Peptide Aptamers

To identify peptide aptamers (PAs) that specifically recognize and bind mutant p53, a modified yeast two hybrid screening was employed using as bait the core domain (CD), between amino acids 74 and 298, of p53 R175H hot spot mutant. A random peptide aptamer library was generated as a prey, by inserting degenerated oligonucleotides encoding 16 amino acid aptamers, into the catalytic site of Escherichia coli Thioredoxin A (Trx) (See Methods). The library construct (pJG4-5-TNV16mers) contains an expression cassette where the Trx cDNA is fused with an N-terminal HA tag and with a C-terminal nuclear localization sequence from SV40 virus large T antigen (NLS) and a VSV tag (TNV, schematically represented in FIG. 1a) (Gostissa, M. et al. The transcriptional repressor hDaxx potentiates p53-dependent apoptosis. J. Biol. Chem., 2004, 279:48013-23). In the primary screening, about 9 million clones were plated and screened according the standard procedures (Sandy P., Gostissa M., Fogal V., Cecco L. D., Szalay K., Rooney R. J., Schneider C., Del Sal G. p53 is involved in the p120E4F-mediated growth arrest. Oncogene, 2000, 19:188-199). After the secondary screening, fifty-three PAs were identified as interactors of the core domain of p53 R175H. These interactions were further confirmed in a tertiary screening, by using as bait p53 R175H or wild-type p53, from amino acid 74 to 393. This analysis showed that 9 aptamers were able to bind mutant p53 R175H, but not wild-type p53, and therefore were chosen for further studies. One peptide aptamer B6 (Seq. ID No 11) that did not show any interaction with mut-p53 was used in all the experiments as negative control. Sequence analysis revealed that the variable region of most aptamers is enriched in hydrophobic amino acids, even if the primary sequences of these peptides do not show any significant homology between them, or with sequences annotated in protein databases.

The interaction between mutant p53 and the selected PAs was confirmed by co-immunoprecipitation assays. To this end, constructs encoding the TNV cassettes, containing the selected aptamer, fused to GFP into pLPC expression vector (FIG. 1a) were generated. Experiments were performed in p53-null H1299 cells transiently co-transfected with p53 R175H and PAs, where both proteins efficiently localized in the nucleus. Our results revealed that, with the exception of B6, all identified PAs were able to bind to mutant p53 (FIG. 1b). Aptamers A3 (Seq. ID No 1), A29 (Seq. ID No 2), A60 (Seq. ID No 3) and A79 (Seq. ID No.4) showed a stronger interaction with p53 R175H, and were therefore chosen for further characterization, while aptamer B6 was employed as negative control.

Peptide Aptamers Differentially Bind p53 Family Members

In an attempt to verify whether PAs can interact with different p53 mutants, the inventors performed co-immunoprecipitations with different structural (p53 D281G) or contact (p53 R273H, p53 R248W) mutants upon transient transfection of p53 mutants and aptamers in H1299 cells. As shown in FIG. 2a, PAs efficiently bind these mutants, suggesting that the selected aptamers could recognize a binding motif common to all mutant proteins.

It has been reported that aptamers may lose their ability to bind the target protein when tested as unconstrained molecules (Hoppe-Seyler, F. et al., ref. cit.). To evaluate whether unconstrained PAs retain the ability to bind mutant p53, biotinylated 16mers, were produced and used for in vitro binding experiments with cellular extracts from Sk-Br-3 cells or HT-29 cells, expressing endogenous p53 R175H and R273H respectively (FIG. 2 b). The results clearly show that all the tested peptides, but not a control peptide derived from the sequence of Thioredoxin (C−, see Table 1), bind to both p53 mutants. Due to technical problems in the chemical synthesis of A79, the peptide was redesigned by changing the position of some aa in its primary sequence. The new sequence of biotinylated A79, named sA79, turned out to be the strongest interactor in in vitro binding assays with all p53 mutants tested (FIG. 2 b). A stronger interaction was also observed for sA79, when assayed as peptide aptamer in the context of Trx scaffold, in co-immunoprecipitations performed as previously described with p53 R175H and R273H (FIG. 2c).

Aptamers were selected to bind the core domain of mutant p53 proteins, which should be structurally distorted and dissimilar to that of wild-type p53. Therefore, it was examined whether aptamers could discriminate between mutant and wild-type p53 proteins. Co-immunoprecipitation experiments upon overexpression of PAs in HCT116 cells, which express endogenous wild-type p53, or in Sk-Br-3 cells, revealed that all selected PAs bind stronger to p53 R175H than to wild-type p53 (FIG. 2d).

Next it was examined whether peptide aptamers could recognize the p53 homologue p73. To test this hypothesis HA tagged version of p53-R175H, TAp73α and wild-type p53 were generated and transfected together with GFP-tagged aptamers in H1299 cells followed by co-immunoprecipitation with anti-GFP antibody and western blot with anti-HA antibody. All aptamers were able to interact efficiently with TAp73α (FIG. 2e) and also with p63 (data not shown). Taking together these results demonstrate that the identified aptamers recognize more efficiently p53 mutants, p73α and p63 than wild-type p53.

Modelling of Aptamer Structures and Docking on Mutant p53 R273H and Wild-Type p53

Taking advantage of the restricted degrees of freedom of the PAs conformation when inserted in the thioredoxin scaffold, the conformation of Pas through in silico analysis was modelled. For the docking of PAs onto mutant p53, the X-ray structure of superstable p53R273H, which contains four stabilizing mutations (M133L, V203A, N239Y and N268D) (PDB CODE: 2BIM), has been used (Joerger, A. C., et al. 2004, ref. cit.). At present this is the only crystal structure available for mutant p53. Indeed, despite the good knowledge of the structure of the wt p53 core domain, there are only few structural information about the core domains of p53 mutants, due to their high thermodynamic instability. In our docking analysis, all the stabilizing mutations have been reversed using Swiss-Pdb Viewer program (see Methods). Two regions of p53 R273H were predicted to be important for docking of all the PAs considered (Table 2). They involve the N-terminus of CD and the loop-sheet-helix (LSH) motif, which establish a large number of polar interactions with the aptamers, particularly T102, L130 and N131 that interact with four out of five PAs (Table 2). A29 and sA79 also form extensive hydrophobic interactions with Leu11, Phe113, Tyr126, Pro128 and Thr102, Tyr103, respectively. Other residues predicted to be contacted by some aptamers comprise L111-H115 (L1), Y126-K132 (S2/S2'), K164-H273 (L2-H1). Therefore docking analysis performed with the available crystal structure of p53R273H, with all the stabilizing mutations reversed to the original residues predicted that all PAs would bind the same region of the mutant p53 core domain. Moreover, some amino acids predicted to contact PAs are located in a region previously reported to be affected by structural changes in p53R273H (Wong, K. B., DeDecker, B. S., Freund, S. M., Proctor, M. R., Bycroft, M. and Fersht, A. R. Hot-spot mutants of p53 core domain evince characteristic local structural changes. *Proc. Natl. Acad. Sci. USA,* 1999, 96:8438-8442) suggesting that these alterations may be responsible for the ability of PAs to discriminate between mutant and wt p53.

Interestingly, PAs that interact with mutant p53 are also able to bind efficiently to p73 and p63. This may be due to the presence of a structural element in TAp73 similar to that recognized by PAs in mutant p53.

As reported in Table 2, the predicted interactions identified two regions of p53 R273H predicted to be important for docking of all PAs.

TABLE 2

Summary of Docking Analysis results

| p53R273H | APTAMERS | | | | |
|---|---|---|---|---|---|
| | A3 | A29 | A60 | A79 | sA79 |
| Gln100 | K2 (b) | — | L5 (b) | — | E6 (b + s) |
| Lys101 | — | — | G7 (b) | V16 (t) | G9 (b) |

TABLE 2-continued

Summary of Docking Analysis results

| p53R273H | APTAMERS | | | | |
|---|---|---|---|---|---|
| | A3 | A29 | A60 | A79 | sA79 |
| *Thr102 | — | R6 (s) | R11 (s) | W13 (s) | S7 (s) W5 (h) |
| Tyr103 | — | — | — | — | Y14 (h) |
| Gln104 | — | — | V12 | — | E10 (b + s) |
| Leu111 | — | P5 (h) | — | — | — |
| Phe113 | — | V3 (b + h) P5 (h) | — | — | — |
| His115 | — | G1 (b) | — | — | — |
| Tyr126 | — | V3 (h) P5 (h) | — | — | — |
| Pro128 | — | V3 (h) | — | — | — |
| Ala129 | — | Y9 (b) | I1 (t) | — | — |
| *Leu130 | R11 (s) | Q8 (s) | — | E11 (b) | — |
| *Asn131 | K2 (s) | T7 (b) | — | E11 (s) | E6 (b) |
| Lys132 | — | — | — | D8 (s) | — |
| Lys164 | — | Q8 (s) | — | G10 (b) | — |
| Gln165 | C6 (s) | — | — | — | — |
| Asp268 | — | R6 (s) | — | W13 (s) | — |
| Glu271 | — | — | — | E11 (s) | — |
| His273 | — | — | — | D8 (s) | — |
| Gln285 | Q5 (s) | — | — | — | — |

In the first left column, there are reported the residues of p53 R273H contacted by some peptide aptamers. In all the other columns there are reported the residues of every aptamers that contact residues of p53 R273H. Residues of p53 R273H are reported in three-letter code, residues of the aptamers are reported in one-letter code and the bold letter represent the aptamers residues more important for the binding to mutant p53. Numbers represent the aa position in the p53 protein or in the aptamers sequences. Residues of p53 marked with asterisks are the ones contacted by at least 3 out of 5 aptamers. Residues that establish interactions: hydrophobic (h) or polar (b, s, t). Part of the residues that establishes the H-bond interactions: (b) backbone, (s) side chain, (t) N- or C-terminal.

Peptide Aptamers Interfere with Mutant p53 Transactivating Functions

One of the mechanisms proposed to explain the oncogenic function of mutant p53 is the ability to alter transcription of different genes. In particular, p53 D281G was reported to induce c-myc promoter (Weisz L., and Rotter V. ref. cit.). In order to test a possible inhibition of mutant p53 transactivation activity by PAs, luciferase assays were performed in p53-null MG63 cells, transiently transfected with a c-Myc-Luc reporter and p53 D281G. As shown in FIG. 3a, all aptamers significantly impaired the transactivation activity of mutant p53, while B6 did not showed any effect. Furthermore, we also tested whether synthetic peptides, free from the Trx scaffold, could display similar effects on mutant p53 transactivation. To this end, a fluoresceinated version of sA79 peptide (FsA79) was synthesized and used in transfection experiments. The effect of this peptide on the induction of Egr-1, which was shown to be a target of mutant p53 transactivation, was tested. Luciferase assays were performed treating cells with FsA79 upon co-transfection of p53 R175H or R273H with EGR1-Luc reporter (Weisz, L., and Rotter, V., ref. cit.). The results indicated that FsA79 inhibits the transactivation activity of both mutants (FIG. 3b). As shown above, all PAs recognized wild-type p53 very weakly (FIG. 2d). To test if aptamers may also affect the transactivation activity of wild-type p53, luciferase assays co-transfecting wild-type p53 with PAs and a p21-luc reporter were performed in H1299 cells. Under these conditions aptamers did not affect the transcriptional activity of wild-type p53 (FIG. 3c). Interestingly, similar results were obtained when the effect of PAs on transactivation of p21-Luc by p73 was tested (FIG. 3d). Moreover, all aptamers, but A60, do not significantly affect the transactivation activity of both wild-type p53 and p73 on a Bax-Luc reporter (FIG. 3e and FIG. 3f). Taking together these results indicate that PAs that specifically bind mutant p53 interfere with its transactivation ability but do not alter the activity of wild-type p53 and p73.

Peptide Aptamers Trigger Apoptosis Specifically in Mutant p53 Bearing Cells

The presence of mutant p53 has been associated with increased cell proliferation and survival (Sigal, A. and Rotter, V. ref. cit.), it was therefore analyzed the effect of the overexpression of PAs on cell cycle and apoptosis of cells bearing endogenous mutant p53. DNA content was measured and integrity by flow cytometry in two different breast cancer cell lines, Sk-Br-3 and MDA-MB-468, expressing endogenous p53 R175H and R273H respectively, upon transfection of PAs fused to GFP in pLPC vectors (see FIG. 1a) were measured. To specifically evaluate the effect on cells expressing the aptamers, propidium-iodide staining was measured only in the GFP positive population. In this way, a sub-G1 peak, indicative of apoptotic cell death, was detected in both tumor cells expressing PAs that bind mutant p53 (FIG. 4a) while no relevant changes in other cell cycle parameters were observed (FIG. 4b). A similar analysis performed in p53-null H1299 cells and U2OS cells, expressing endogenous wild-type p53, demonstrated that PAs did not affect cell cycle profile in these cell lines (FIG. 4a), indicating that the presence of mutant p53 correlate with the observed effect. Apoptotic cell death, induced by the two strongest mutant p53 interacting aptamers (A29 and sA79), was further confirmed in Sk-Br-3 and MDA-MB-468 cell lines by evaluating Annexin-V staining of GFP positive cells and PARP cleavage. As negative controls, pLPC-GFP or the B6 aptamer, unable to bind p53, were used. Analysis by flow cytometry showed approximately 30% of AnnexinV positive cells upon transfection with the selected aptamers, compared to less than 15% in control cells (FIGS. 4c and 4d). The evident increase of the cleaved p85 fragment of PARP-1 in Sk-Br-3 cells observed in cells transfected with A29 or sA79, finally confirmed the ability of these aptamers to induce apoptosis (FIG. 4c).

The effect of aptamers was compared to that of commonly used anticancer drugs and also it was evaluated whether the concurrent expression of PAs and drug treatment could improve apoptosis. Sk-Br-3 cells were transfected with A29, sA79 or B6 aptamers, treated with two different doses of Etoposide or left untreated and assayed for the sub-G1 DNA content as described above. Interestingly, it was observed that expression of mutant p53 interacting aptamers is sufficient to induce an apoptotic response comparable to that observed upon drug treatment alone (FIG. 4e). No further increment of cell death was evidenced when cells transfected with PAs were simultaneously exposed to Etoposide (FIG. 4e, grey and white bars). Using the same cell lines we also compared the effect of aptamers to that of PRIMA-1, a small molecule known to induce apoptosis in cells expressing mutant p53 (Bykov, V. J., Issaeva, N., Shilov, A., Hultcrantz, M., Pugacheva, E., Chumakov, P., Bergman, J., Wiman, K. G. and Selivanova, G. Restoration of the tumor suppressor function to mutant p53 by a low-molecular-weight compound. *Nature Med.*, 2002, 8:282-288.). Sk-Br-3 cells transfected with B6, which is unable to induce apoptosis, and treated with 100 μM PRIMA-1 for 20 hours were compared with cells transfected with A29 or sA79. Also in this case, the sub-G1 peak observed in cells expressing peptide aptamers was comparable to that induced by PRIMA-1 (FIG. 4f). These data therefore indicate that these peptide aptamers can induce apoptosis in cells expressing mutant p53 to a level comparable to therapeutic drugs.

The invention claimed is:

1. An isolated molecule comprising a peptide, wherein said peptide is selected from the group consisting of peptides having the sequences AKYCQCAAKVRVTAAM (Seq.ID.No:1), GPVVPRTQYMSLAFGW (Seq.ID.No:2), IQITLTGWSARVTTSG (Seq.ID.No:3), VWAESCDCGEYWRYV (Seq.ID.No:4), DVADWESCGEYWCYRV (Seq.ID.No:5), QAGSGREKCQHAAYLS (Seq.ID.No:6), ARTDTAVVHVCDSGRQ (Seq.ID.No:7), QQSRGRCPSCIPEAAS (Seq.ID.No:8), PGKLIRVSENMSSALG (Seq.ID.No:9), and TPEGLDVALAVAAYSV (Seq.ID.No:10).

2. The isolated molecule according to claim 1, wherein the peptide further comprises biochemical modifications suitable to stabilize, compartmentalize or localize the same.

3. The isolated molecule according to claim 1, wherein the peptide further comprises chemically modified amino acids and/or uncommon and/or non-natural amino acids.

4. The isolated molecule according to claim 1, wherein the peptide at C- or N-terminus is fused with further sequences of amino acids and/or is bearing chemical or biochemical modifications.

5. The isolated molecule according to claim 4, wherein the peptide is fused with penetrating peptides.

6. The isolated molecule according to claim 1, wherein the peptide is comprised in a protein scaffold.

7. The isolated molecule according to claim 6, wherein said protein scaffold is selected from the group consisting of thioredoxin and human stefin.

8. A pharmaceutical composition comprising as active principle at least one isolated molecule according to claim 1, in combination with pharmaceutically acceptable excipients, diluents and/or delivery systems of the active principle, wherein said composition is for systemic and/or local administration.

* * * * *

SEQUENCE LISTING

```
<160> NUMBER OF SEQ ID NOS: 11

<210> SEQ ID NO 1
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 1

Ala Lys Tyr Cys Gln Cys Ala Ala Lys Val Arg Val Thr Ala Ala Met
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 2

Gly Pro Val Val Pro Arg Thr Gln Tyr Met Ser Leu Ala Phe Gly Trp
```

```
<210> SEQ ID NO 3
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 3

Ile Gln Ile Thr Leu Thr Gly Trp Ser Ala Arg Val Thr Thr Ser Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic

<400> SEQUENCE: 4

Val Trp Ala Glu Ser Cys Asp Asp Cys Gly Glu Tyr Trp Arg Tyr Val
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 5

Asp Val Ala Asp Trp Glu Ser Cys Gly Glu Tyr Trp Cys Tyr Arg Val
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 6

Gln Ala Gly Ser Gly Arg Glu Lys Cys Gln His Ala Ala Tyr Leu Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 7
```

Ala Arg Thr Asp Thr Ala Val Val His Val Cys Asp Ser Gly Arg Gln
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 8

Gln Gln Ser Arg Gly Arg Cys Pro Ser Cys Ile Pro Glu Ala Ala Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 9

Pro Gly Lys Leu Ile Arg Val Ser Glu Asn Met Ser Ser Ala Leu Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 10

Thr Pro Glu Gly Leu Asp Val Ala Leu Ala Val Ala Ala Tyr Ser Val
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(16)
<223> OTHER INFORMATION: PEPTIDE

<400> SEQUENCE: 11

Gln Arg Gly Leu Tyr Cys Ser Cys Val Thr Asn Gln Asn Ala Glu Val
1               5                   10                  15